United States Patent [19]

Sonne et al.

[11] Patent Number: 5,416,329
[45] Date of Patent: May 16, 1995

[54] APPARATUS FOR COUNTING LIQUID SCINTILLATION SAMPLES

[75] Inventors: Vesa Sonne, Vanhalinna; Kauko Lehtinen, Raisio; Tapio Yrjönen, Turku, all of Finland

[73] Assignee: Wallac Oy, Turku, Finland

[21] Appl. No.: 300,084

[22] Filed: Sep. 2, 1994

Related U.S. Application Data

[63] Continuation of Ser. No. 969,281, Jan. 8, 1993, abandoned.

[51] Int. Cl.⁶ .................... G01N 35/10; G01T 1/204
[52] U.S. Cl. ..................................... 250/364; 250/328
[58] Field of Search ................... 250/328, 362, 364

[56] References Cited

U.S. PATENT DOCUMENTS

| | | | |
|---|---|---|---|
| 3,038,078 | 6/1962 | Kern | 250/328 |
| 3,654,472 | 4/1972 | Hof et al. | 250/328 X |
| 3,855,473 | 12/1974 | Burgess et al. | 250/328 |
| 3,898,457 | 8/1975 | Packard et al. | 250/328 |
| 3,911,274 | 10/1975 | Roos et al. | 250/328 |
| 4,454,939 | 6/1984 | Kampf et al. | 250/328 X |

FOREIGN PATENT DOCUMENTS

WO89/12838 12/1989 WIPO .................. 250/328

OTHER PUBLICATIONS

Warner et al. 'A New Design for a Liquid Scintillation Counter for Micro Samples Using Flat-Bed Geometry', 2211 International Journal of Applied Radiation and Isotopes, 36 (1985) Oct., No. 10, Oxford, Great-Britain.

*Primary Examiner*—Constantine Hannaher
*Assistant Examiner*—Edward J. Glick
*Attorney, Agent, or Firm*—Adduci, Mastriani, Schaumberg & Schill

[57] ABSTRACT

A device for counting liquid scintillation samples which can count a single sample or several samples simultaneously. A transport system moves samples from a storage section to a counting section. The samples are placed on sample plate holders to assist the transport system in movement of the sample from the storage section to the counting section.

7 Claims, 11 Drawing Sheets

APPARATUS FOR COUNTING LIQUID SCINTILLATION SAMPLES

This application is a continuation of application Ser. No. 07/969,281 filed Jan. 8, 1993 (now abandoned).

BACKGROUND OF THE INVENTION

Liquid scintillation counters are commonly used to measure the count rate or activity of samples containing low energy beta particles or corresponding particles emitting radionuclides such as tritium and carbon-14.

The range of the low energy beta particles in the sample is generally a few tens of micrometers at the most. As a consequence, the sample to be measured has to be placed in direct contact with a scintillation medium by dissolving or suspending the sample within the liquid scintillation medium in a container so that the emitted beta particles can interact with the molecules of the liquid scintillation medium. The medium comprises a solvent or solvents and a solute or solutes present in a few percent by weight of the solution. In this interaction process, most of the kinetic energy of the interacted beta particle is absorbed by the solvent and then transferred to the solute which emits scintillation photons in an amount proportional to the energy of the interacted beta particle. These scintillation photons are detected by two photomultiplier tubes simultaneously producing electric pulses. The sum pulse height is proportional to the energy of the interacted beta particle.

The conventional liquid scintillation counters have been designed to measure samples which are in sample vials with the scintillation medium. The volume of the sample vial is typically 6 or 20 milliliters. The sample vials are placed in elongated sample holders, which have a plurality of compartments for individual sample vials. A plurality of types of sample vial holders may include holders characterized by the size of the sample vials they are adapted to contain. The sample vial holders are placed on the conveyor of the automatic sample changer system of the liquid scintillation counter.

Because the conventional liquid scintillation counters have been designed to measure samples in vials, whose volumes are up to 20 milliliters, difficulties will be encountered when the sample volumes are only a few hundred microliters or less. Typically, these kinds of samples with medical or biological interest are prepared in small tubes, which have been inserted into normal vials. In addition, the handling of separate sample vials is very time consuming and includes a potential risk of setting the sample vials in incorrect order into the sample holders. The sample changing mechanism of such an instrument is also rather complicated, because the vial must be removed from the sample plate holder and must be positioned into a light tight radiation detection chamber and, after counting, it must be returned back to the sample holder.

In addition to the above mentioned conventional liquid scintillation counters, one special purpose liquid scintillation counter exists, identified by the trade name 1205 Betaplate, and manufactured by Wallac Oy, Finland. Originally this instrument was designed to measure liquid scintillation samples deposited on a filter mat and sealed into a plastic bag with a small amount of scintillation liquid. The maximum diameter of these sample spots is 10 millimeters and the distance between the center points is 15 millimeters. A total of 96 sample spots are arranged in a 6×16 matrix format. The Betaplate is provided with 6 detectors, one for each row, thus 6 samples will always be measured simultaneously.

The Betaplate has been developed to measure samples deposited in a type of multi-well sample plate comprising 96 separate sample wells arranged in the same 6×16 format and with the same 15 millimeter distance between the center points as in the filter mats. The maximum height of this multi-well sample plate is 7.5 millimeters and the maximum volume of the sample well is limited to 400 microliters.

Thus the Betaplate is applicable for measuring 6 samples simultaneously deposited on filter mats or multi-well sample plates having only one format. Unfortunately, in practice, there is a need for multi-well sample plates with various formats and well volumes. In addition, a six detector liquid scintillation counter will be too expensive in some applications due to the relatively small amount of samples to be measured.

SUMMARY OF THE INVENTION

The present invention will show a new apparatus adapted to measure simultaneously one or several liquid scintillation or corresponding samples in sample plates with various heights. The sample plates belong to a preselected assortment of different multi-well sample plate types, each having a characteristic two dimensional array of sample wells or vials.

One group of multi-well sample plates belonging to the preselected assortment consists of 96-well sample plates having eight rows of wells arranged in twelve columns with 9 millimeters distance between the center points of the wells. The typical volumes of the sample wells of such 96-well sample plates are 200–400 microliters depending on the height of the plate. Another group of suitable multi-well sample plates consists of 24-well sample plates having four rows of wells arranged in six columns with 18 millimeters distance between the center points of the wells. Depending on the height of plates, the volume of the wells of such a 24-well sample plate arrangement is, for example, 1–5 milliliters. Thus the apparatus according to the present invention has been designed to measure liquid scintillation samples, the volume of which is from a few microliters up to several milliliters.

The apparatus according to the present invention comprises a random access storage compartment for sample plate holders including a plurality of types, each adapted for carrying multi-well sample plates of different types having a preselected assortment. The random access storage compartment may contain any combination of different sample plate holder types where sample holders include all variations from one sample to a full load of samples.

The apparatus according to the present invention is provided with a transport system or transportation means for taking sample plate holders including a plurality of types of sample plates, one at a time, from the random access sample plate holder storage compartment to a measuring station provided with 1, 2, 3 or 6 detectors and returning a sample plate holder, after measurement, back to the storage compartment.

The detectors consist of a pair of in coincidence or simultaneously operating, vertically disposed, photomultiplier tubes mounted in two detector assemblies. The upper detector assembly is adapted to move in a vertical direction in order to enable various heights of the multi-well sample plates to be accommodated. Both detector assemblies are provided with aperture plates having various circular apertures for different well diameters of various type multi-well sample plates.

The detector places are arranged in 2 rows with 3 columns having 36 millimeters spacing between the center points. When the apparatus is provided with one detector, the detector is positioned on the first column of the first row. When the apparatus is provided with 2 detectors, the detectors are positioned on the first columns of the first and the second row. If the apparatus is provided with 3 detectors, all 3 detectors are placed on the first row. This provides, for example, the following matrix format and well separation of multi-well sample plates when the apparatus comprises 1, 2, 3 or 6 detectors:

| number of wells | rows | columns | separation |
| --- | --- | --- | --- |
| 96 | 8 | 12 | 9 mm |
| 24 | 4 | 6 | 18 mm |
| 6 | 2 | 3 | 36 mm |

In general, if the distance between the center points of the detector places is d, then the allowed distances of the center points of the sample wells should be d/n, where n=1, 2, 3, . .

The sample plate transportation system of the apparatus according to the present invention is suited for general use in analytical instrumentation when it is required to transport multi-well sample plates provided with different heights and different two-dimensional array of sample wells from a random access storage compartment to an analytical measuring station and then returning such sample plates to the compartment.

DETAILED DESCRIPTION

Figure 1:
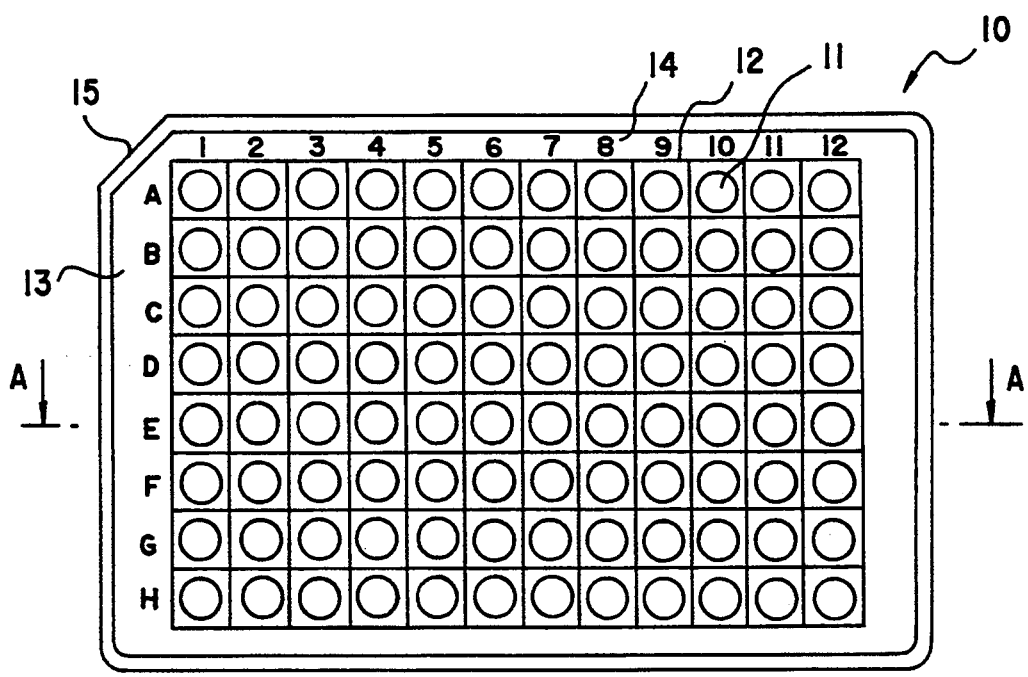
FIG. 1 shows a top view of a multi-well sample plate having 96 sample wells in a 8×12 matrix format.

In FIG. 1 there is shown a top view of one of the multi-well sample plates 10 comprising 96-wells 11 in 8×12 matrix format. The plate 10 being produced by a vacuum thermoforming process from transparent material, for example, polyethylene terephthalate or other thermoformable plastic. The separation between the wells is 9 millimeters and the maximum diameter of the wells is 7.8 millimeters. The plate is provided with printed lines 12 to prevent the travelling or movement of the light between the wells. The plate is provided with lettering 13 for row identification and numbering 14 for column identification. The corner of the sample plate, which is closest to the well A1 (row A, column 1), is provided with a cut-off beveled edge 15 to force the user to place the sample plate in a correct position with respect to the sample plate holder shown in FIG. 5.

Figure 2:
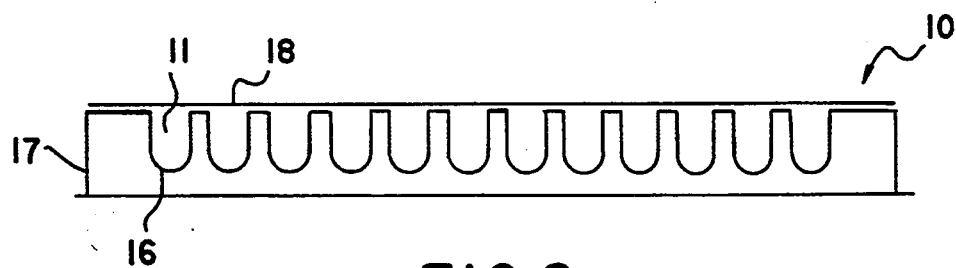
FIG. 2 shows a cross-sectional view of a multi-well sample plate having 96 sample wells in a 8×12 format, the view taken along line A—A in FIG. 1.

FIG. 2 shows a side view of the 96-well sample plate taken along line A—A in FIG. 1. The bottoms of the wells 16 are rounded. The shape of the bottoms can also be flat or any other shape. The depth of the wells is less than the height of the side wall 17 of the plate. The plate can be sealed by an adhesive tape 18 or by a heat sealer apparatus well known in the art.

Figure 3:
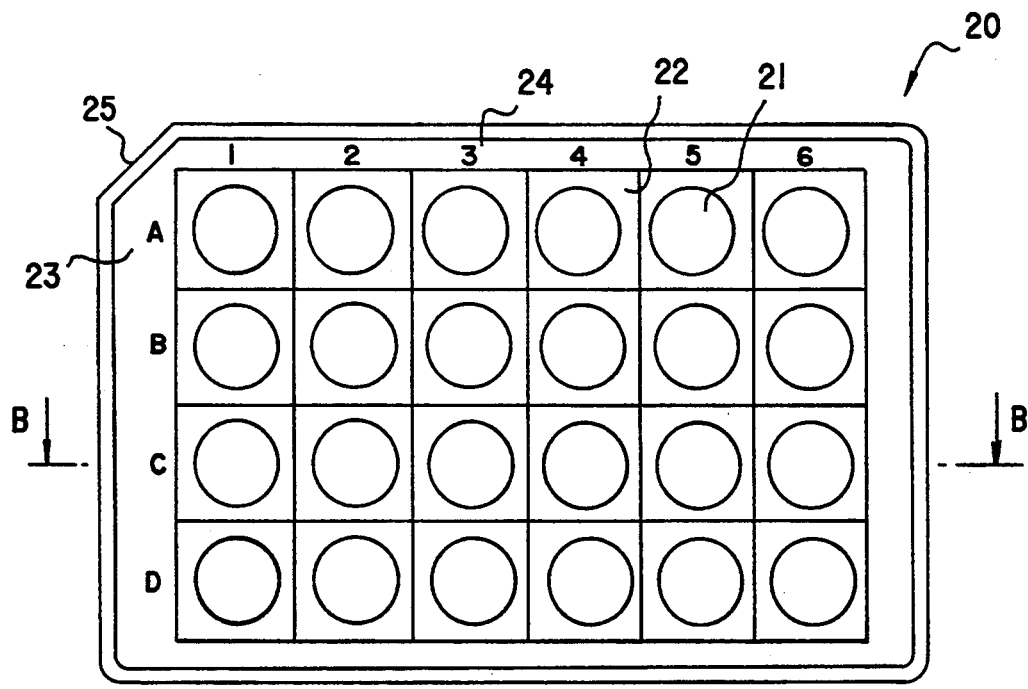
FIG. 3 shows a top view of a multi-well sample plate having 24 sample wells in a 4×6 matrix format.

In FIG. 3 there is shown a top view of one of the multi-well sample plates 20 provided with 24 wells 21 in a 4×6 matrix format. The plate being produced by a vacuum thermoforming process from transparent material, for example polyethylene terephthalate or other thermoformable plastic. The separation between the wells is 18 millimeters and the maximum diameter of the wells is 13.2 millimeters. The plate is provided with printed lines 22 to prevent the travelling or movement of the light between the wells 21. The plate is provided with lettering 23 for row identification and numbering 24 for column identification. The corner of the sample plate, which is closest the well A1 (row A, column 1), is provided with a cut-off beveled edge 25 to force the user to place the sample plate in a correct position with respect to the sample plate holder shown in FIG. 7.

Figure 4:
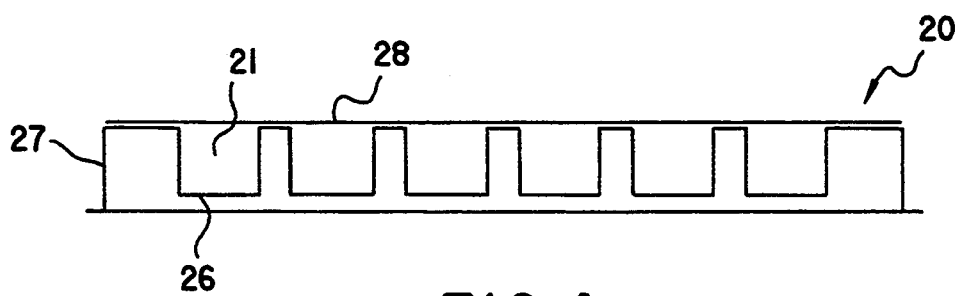
FIG. 4 shows a cross-sectional view of a multi-well sample plate having 24 sample wells in a 4×6 format the view taken along line B—B in FIG. 3.

FIG. 4 shows a side view of the 24-well sample plate taken along line B—B in FIG. 3. The bottoms of the wells 26 are flat. As in the example of FIG. 2, the bottoms can be rounded or any other shape. The depth of the wells is less than the height of the side wall 27 of the plate. The plate can be sealed by an adhesive tape 28 or by a heat sealer apparatus well known in the art.

Figure 5:
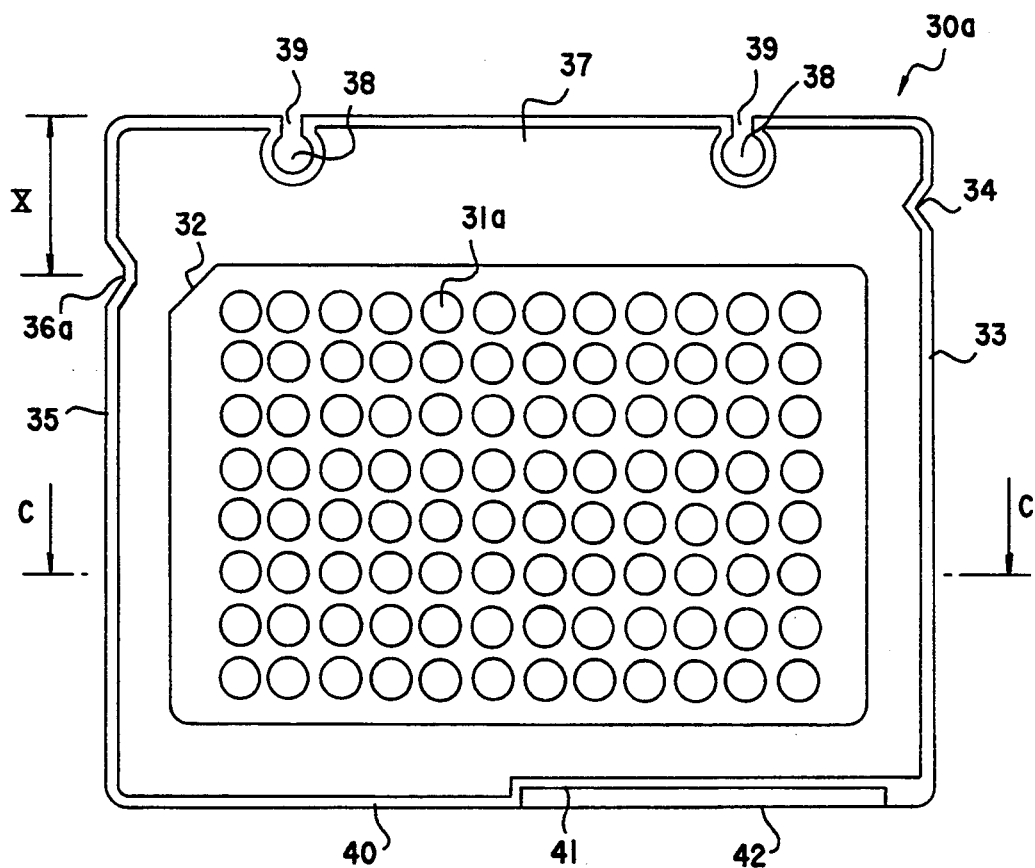
FIG. 5 shows a top view of a sample plate holder for 96-well sample plates.

FIG. 5 shows a sample plate holder 30a suitable for the 96-well sample plates 10 shown in FIG. 1 and 2. The plate holder is produced by an injection molding process from a light-impermeable material having a high degree of reflectivity for scintillation light, for example, a special-grade polycarbonate plastic containing a high amount of white pigment.

Figure 6:
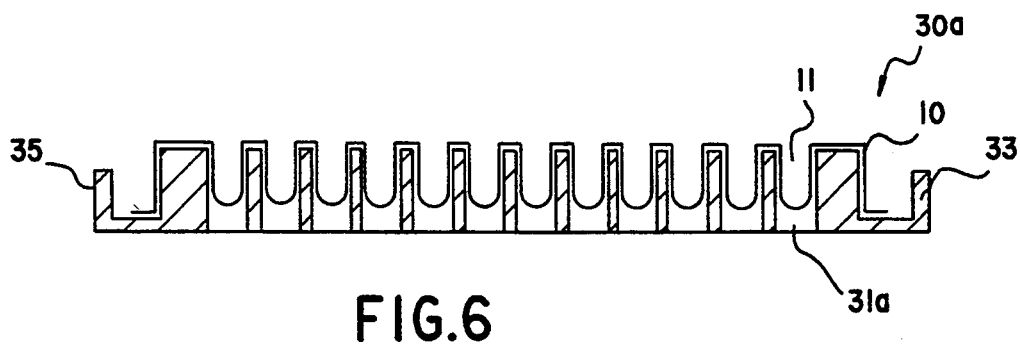
FIG. 6 shows a cross-sectional view of a sample plate holder for 96-well sample plates taken along line C—C in FIG. 5.

FIG. 6 shows a side view of a 96-well sample plate holder 30a taken along line C—C in FIG. 5 with a 96-well sample plate 10. The sample plate holder 30a is provided with circular through holes 31a for the wells 11 of the sample plate 10. The sample plate holder is provided with a cut-off or bevel corner 32 to engage the sample plate in a single position. The right side 33 of the sample plate holder 30 is provided with a slot 34 and the left side 35 of the sample plate holder 30a is provided with another slot 36a. The purpose of these slots 34 and 36a will be explained later. The rear side 37 of the sample plate holder 10 is provided with two identical pivot holes 38 from its top to its bottom with open slits 39. The x-y-transportation system comprises a transportation block provided with two vertical positioned pivots which are received in or fit to said pivot holes of the sample plate holders. The front side 40 of the sample plate holder 10 is provided with an indent means 41 for carrying or otherwise supporting a detachable support plate 42, on which can be attached at least one bar code label.

Figure 7:
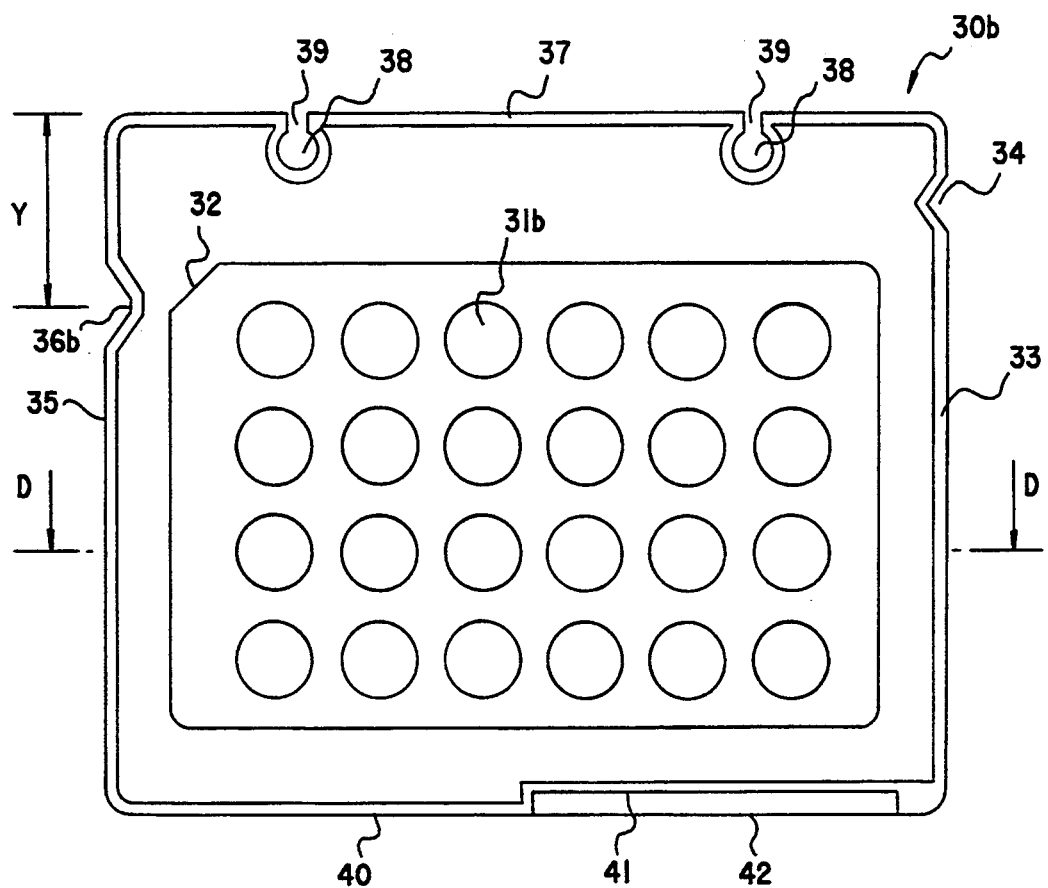
FIG. 7 shows a top view of a sample plate holder for 24-well sample plates.

FIG. 7 shows a sample plate holder 30b suitable for a 24-well sample plates 20 shown in FIG. 3 and 4 and the like produced by an injection molding process. The holder is made from a light-impermeable material having a high degree of reflectivity for scintillation light. An example of the material would be a special-grade polycarbonate plastic containing high amounts of white pigment.

The sample plate holder 30b is provided with circular through holes 31b for the wells 21 of the sample plate 20. The sample plate holder is provided with a cut-off or bevel corner 32 for engagement with the sample plate in a single position. The right side 33 of the sample plate holder 30 is provided with a slot 34 and the left side 35 of the sample plate holder 30b is provided with another slot 36b. The purpose of these slots 34 and 36b will be explained later. The rear side 37 of the sample plate holder 10 is provided with two identical pivot holes 38 from the top to the bottom of the holder. The holes are provided with open slits 39. The x-y-transportation system comprises a transportation block provided with two vertically positioned pivots, which are received in and fit to said pivot holes of the sample plate holders. The front side 40 of the sample plate holder 10 is provided with an indent means 41 for carrying or otherwise supporting a detachable support plate 42, on which can be attached at least one bar code label.

The outer portions of the sample plate holder 30a for 96-well sample plates 10 and the sample plate holder 30b for 24-well sample plates 20 are identical except the distance of slots 36a and 36b from the rear surfaces 37 marked "X" and "Y" in FIGS. 5 and 7, respectively. The control means of the apparatus will use this difference in distance in order to distinguish the two sample plate holders for the two types of multi-well sample plates.

Figure 8:
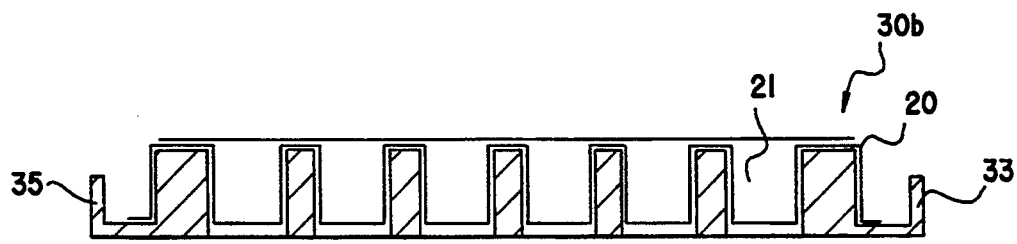
FIG. 8 shows a cross-sectional view of a sample plate holder for 24-well sample plates taken along line D—D in FIG. 5.

FIG. 8 shows a side view of a 24-well sample plate holder 30b taken along line D—D in FIG. 7 with a 24-well sample plate 20.

Figure 9:
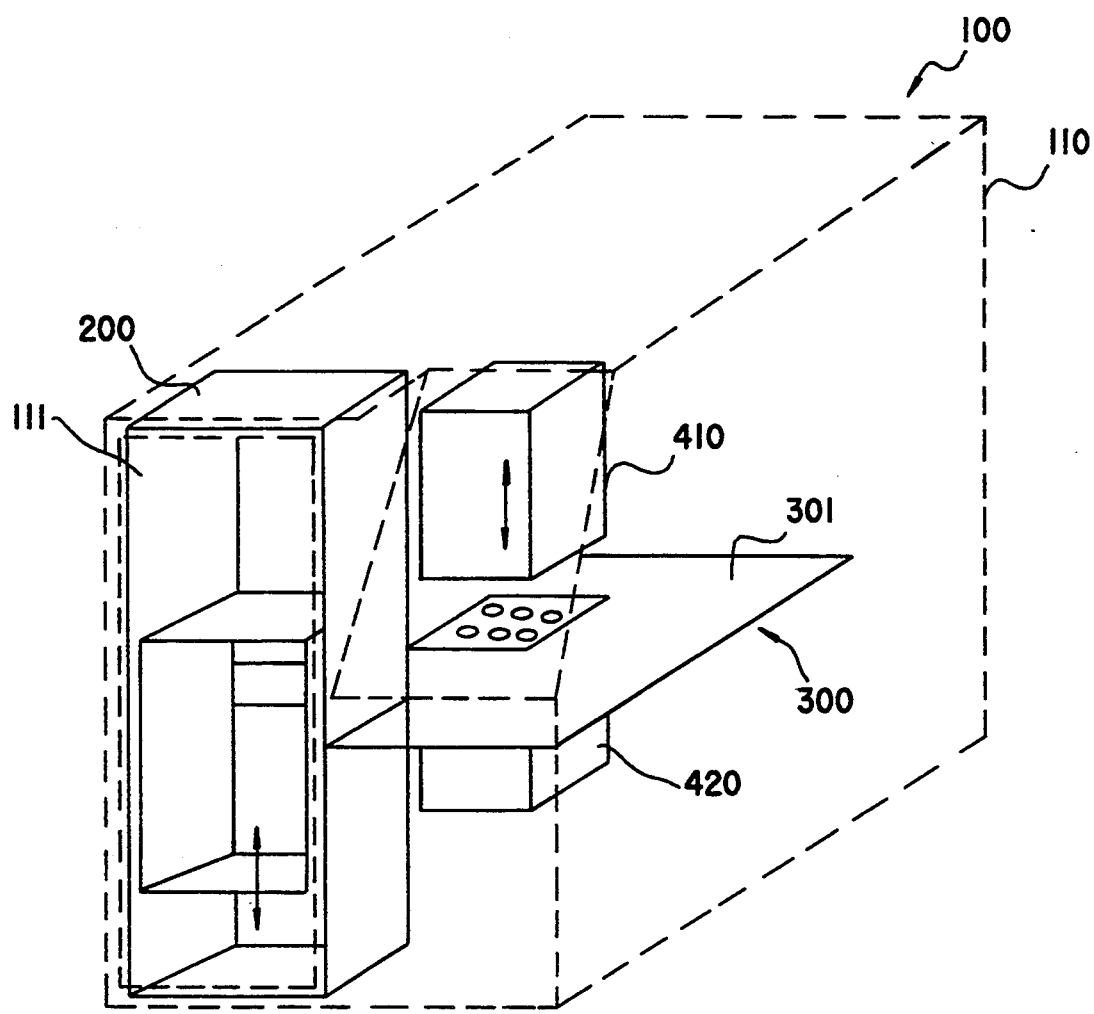
FIG. 9 is a schematic perspective view of the apparatus showing the arrangement of the relationships between the modules of the apparatus.

In FIG. 9 there is shown a schematic perspective arrangement of the relationships between the sample plate holder storage module 200, the horizontal plane 301 of the x-y-transportation unit 300, the upper detector assembly 410 and the lower detector assembly 420. The housing 110 includes a door 111. The apparatus 100 is drawn schematically by dashed lines.

Figure 10:
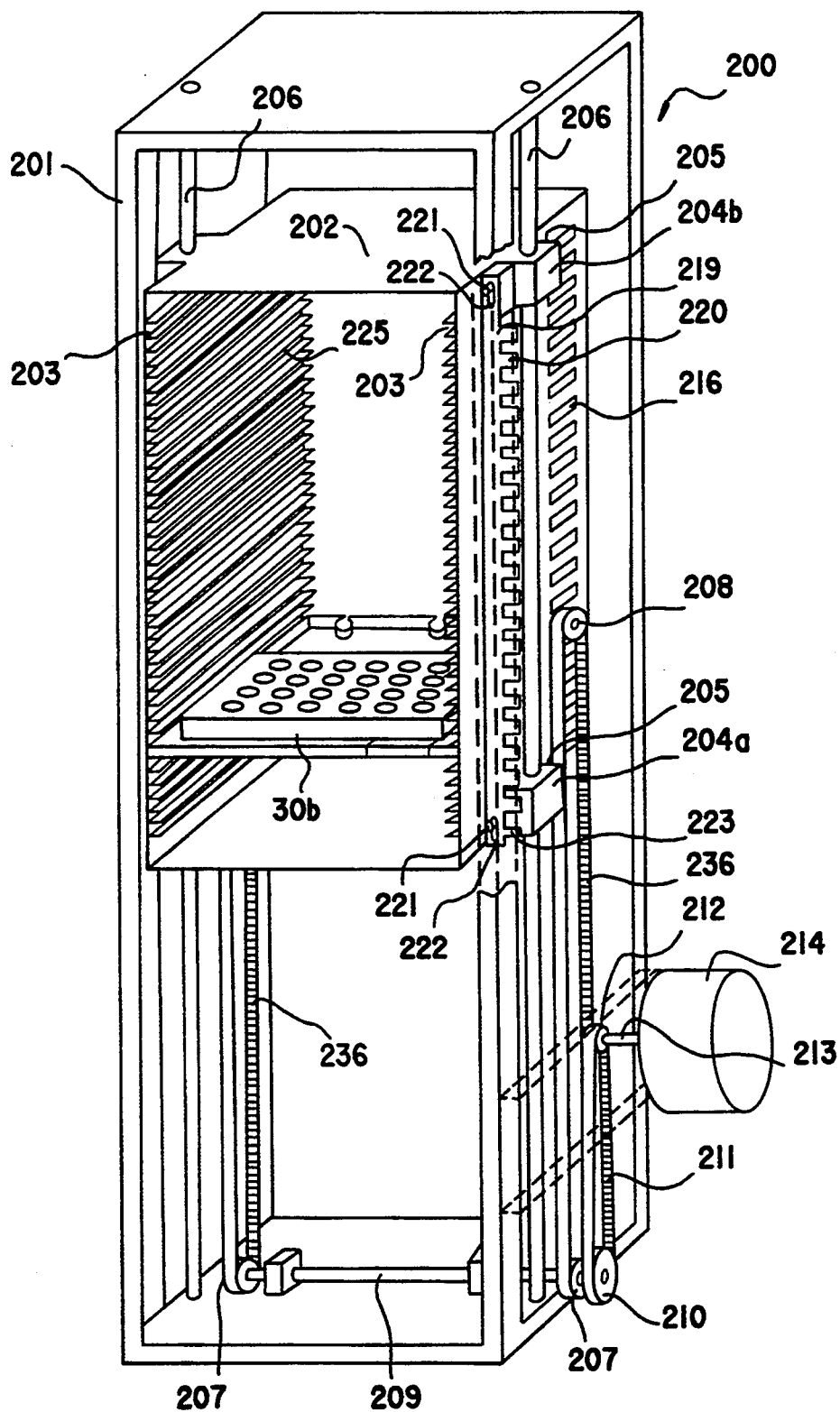
FIG. 10 is a perspective view of the sample plate holder storage compartment of the apparatus.

The storage module 200 for different types of sample plate holders is shown in FIG. 10 and includes a case 201 and a vertically movable storage compartment 202 provided with U-shaped guide members 203. The members 203 are attached on both of the inner sides of the moving storage compartment 202 for supporting sample plate holders 30a or 30b. If the total height of the sample plate holder is less then the separation of the guide members, i.e., 15 millimeters, then 20 sample plate holders can be placed in the storage compartment 202. If the height is between 15 and 30 millimeters, then 10 sample plate holders can be placed in the storage compartment 202. If the height is between 30 and 45 millimeters, then 7 sample plate holders can be placed in the storage compartment. The U-shape of the guide members 203 hinder the movement of the sample plate holders in the vertical direction. It should be noted that the operation may be carried out with any number of sample plate holders in the storage compartment 202, from one to a full or maximum load. Further, any combination of sample plate holder types can be used.

The control means of the apparatus is adapted to stop the storage compartment 202 in such positions that the x-y-transportation means 300 can transport each of the sample plate holders, one at a time, to the counting station, formed by the upper and the lower detector assembly 410 and 420, respectively, and back to the storage compartment 202. This permits an entirely free order for measurement of the sample plates deposited on the sample plate holders in the storage compartment 202.

Two plastic blocks 204a and 204b are attached to each of the outer sides of the vertically moving storage compartment 202. The blocks 204a and 204b have circular openings 205 which fit vertical guide rods 206 attached to the case 201, of the storage module 200, thereby permitting the plastic blocks 204a and 204b and the attached storage compartment 202 to travel vertically along the guide rods 206. To provide the vertical motion, the lower plastic blocks 204a on both side of said storage compartment 202 are connected or attached to cogged belts 236. The belts 236 extend around the cogged wheels 207 and the idler cogged wheels 208. Both cogged wheels 207 are attached with an axle 209 to a cogged wheel 210 which is driven by a cogged belt 211 extending around a driving cogged wheel 212 attached to the shaft 213 of the stepper motor 214 secured to the case 201 of the storage compartment module 200.

When the motor 214 drives the drive wheels 207 in a first direction, the storage compartment 202 is activated to travel upwards along the vertical rods 206. When the motor 214 operates in the opposite direction, the storage compartment 202 is activated to move downwards.

Figure 11:
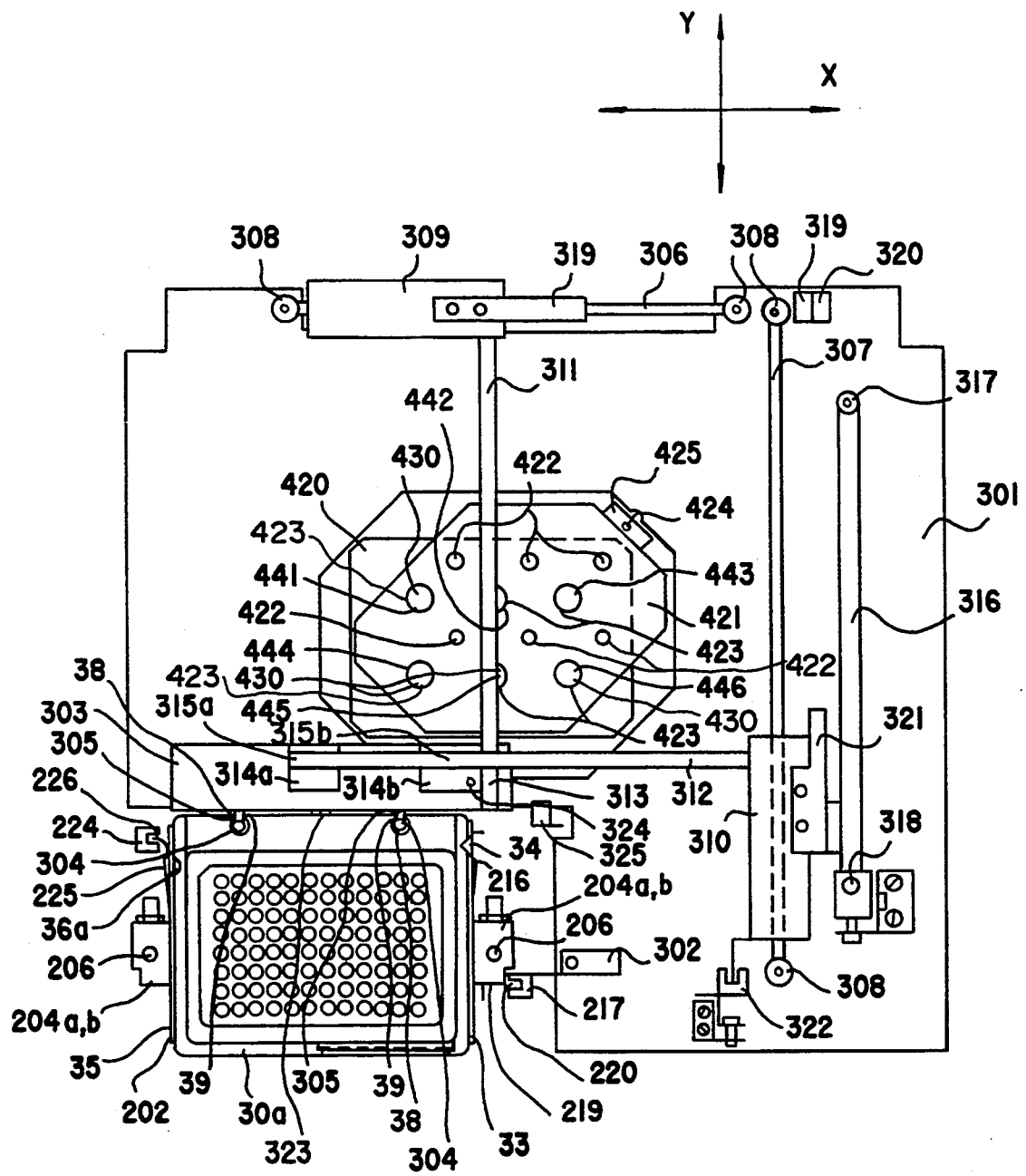
FIG. 11 is a top view of the x-y-transportation system of the apparatus showing the transportation block in the storage compartment position.

FIG. 11 shows that, when a sample plate holder 30b is placed in the storage compartment 202, an angular part of a spring tab 216, attached with each guide member 203 on the right side of the storage compartment 202, is engaged with the slot 34 in the right side 33 of the sample plate holder 30a or 30b so as to secure the sample plate holder in a correct position with respect to the guide members 203.

The sample plate holder storage compartment 202 is provided with a first controller or control means, which controls the vertical positioning of the storage compartment 202. The first control means comprises an electro-optical sensor 217 and a plate 219 with separate tabs 220 corresponding to each of the guide members 203 on the right side of the storage compartment 202. The tab plate 219 is attached to the sample plate holder compartment 202 by two screws 221 through elongated openings 222 so as to permit adjustment of the tab plate. The electro-optical sensor 217 is mounted to the horizontal plate 301 of x-y-transportation module 300 by a vertically adjustable member 302, which permits the vertical adjustment of the position of the sensor. The widths of the tabs 221 are equal except for a single, more narrow tab 223, which corresponds to the lowest sample plate position in the storage compartment 202. The vertical position of the electro-optical sensor 217 and the tab plate 219 is adjusted so that the upper edge of a tab interrupts the light path of the sensor when the lower surface of a sample plate holder 30a or 30b is on the same level as the upper surface of the horizontal plane 301 of the x-y-transportation module 300.

In the case of an uncontrolled situation the storage compartment 202 is moved upwardly by the control system of the apparatus until the electro-optical sensor 217 detects the upper edge of the narrow tab 223. This occurrence informs the control system that the lowest sample plate holder position of the storage compartment 202 is at the same level as the horizontal plane of the 301 x-y-transportation module 300.

The storage compartment 202 is provided with a second control means or controller to detect the type of sample plate holder and vacant positions in the storage compartment 202. The controller comprises an electro-optical sensor 224 attached on the case 201 of the storage compartment module 200 and spring tabs 225 attached on each guide member 203 on the left side of the storage compartment 202. When the sample plate holder 30a or 30b is in the correct position in the storage compartment 202, the left side 35 of the sample plate holder pushes an angular part of spring tab 225 so that the edge 226 of the tab 225 interrupts the light path of the electro-optical sensor 224. This indicates that the corresponding sample plate holder position of the storage compartment 202 is at the same level as the horizontal plane 301 of the x-y-transportation module 300 thereby indicating that the position is occupied. At the same time, this spring tab 225 forces the sample plate holder to abut the right side of the storage compartment 202 securing the correct positioning of the sample plate holders in the lateral direction. Detection of the type of sample plate holder is described later.

In the normal mode of operation, the storage compartment 202 is stopped by the control system of the apparatus when a lower surface of a sample plate holder, which is in a sample plate holder position as determined by guide members 203, is exactly at same level as the upper surface of the horizontal plane 301 of the x-y-transportation module 300. Thereby permitting the x-y-transportation means to move that sample holder to the counting station comprising upper and lower detector assemblies 410, 420 and to return it back to same position in storage compartment 202.

For connecting the sample plate holder to the x-y-transportation means, the sample plate holders 30a and 30b are provided with two pivot holes 38 extending from top to its bottom of the holders and provided with open slits 39 at the rear edge 37 of the sample plate holder.

The x-y-transportation means comprises a transportation block 303 provided with two vertical positioned pivots 304, which are received in or otherwise fit to said pivot holes 38 of the sample plate holders 30a, 30b. The height of these pivots 304 is less than the space between the two nearest or closest sample plate holders 30a, 30b in the storage compartment 202. The pivots 304 are attached to the front of the transportation block by rods 305, which fit to or are otherwise received in the slits 39 of the sample plate holders 30a, 30b. The distance between the pivots 304 of rods 305 is equivalent to the distance between the pivot holes 38 provided with slits 39.

When the apparatus is idle or when the sample plate holder compartment is moving, the transportation block 303 is situated so that the pivots 305, attached thereto, are concentric with the pivot holes 38 of the sample plate holder 30a, 30b. If the apparatus is idle, the storage compartment 202 is stopped so that the pivots 305 are positioned between two sample plate holder positions so as to permit loading and unloading of each sample plate holder. When a connection is made with a sample plate holder, the storage compartment 202 is stopped at the same level as the horizontal plate 301 of the x-y-transportation module. In this position, the pivots 304 attached to the transportation block 304 with rods 305 are engaged with the pivot holes 38 of that sample plate holder. In order to provide for a more rigid connection, the transportation block 303 is provided with a spring tab 323, which pushes the rear side of the sample plate holder.

The x-y-transportation module comprises a horizontal aluminum plate 301 and a transportation means or system attached to the plate 301. The plate is provided with two perpendicular guide rods 306, 307 for the transportation system. One guide rod 306 is parallel to the X-axis and another 307 is parallel to Y axis. Both ends of the rods 306 and 307 are mounted to vertical members 308 attached to the plate 301. The X-guide rod 306 is provided with X-cursor block 309, which can ride along the X-guide rod 306, and Y-guide rod 307 is provided with Y-cursor block 310, which can ride along the Y-guide rod 307. X-cursor block 309 is provided with a rod 311, which is parallel to the Y-axis. Y-cursor block 310 is provided with a rod 312, which is parallel to the X-axis. The vertical position of these rods 311, 312 attached to the cursor blocks 309, 310 from the plate surface 301 differs in that the rods 311, 312 can cross each other. The transportation block 303 is provided with a transverse channel 313 which fits to the rod 311 attached to x-cursor block 309 so that the transportation block 303 can travel in the Y-direction along the rod 311. Two plastic blocks 314a and 314b are attached to the upper surface of the transportation block 303. These blocks 314a and 314b are provided with channels 315a and 315b which connect to the rod 312 attached to Y-cursor block 310 so that the transportation block 303 can travel in the X-direction along said rod 312. Thus, the transportation block 303 is moving in the horizontal plane 301 of the x-y-transportation module 300 with the cursor blocks 309 and 310. The position of the transportation block 303 relative to the zero-position at the horizontal plane 301 corresponds to the vector sum of the positions of the cursor blocks 309 and 310.

The X- and Y-cursor blocks 309, 310 are driven independently of each other along the X- and Y-rods 306, 307 by two stepper motors positioned beneath the horizontal plate 301 (not shown). The Y-cursor block 310 is attached to the cogged belt 316, which extends around the cogged wheel 317 and the idle cogged wheel 318. The cogged wheel 317 is attached directly to the shaft of the stepped motor. The X-cursor block 309 is driven in similar way, the driving system (not shown) is positioned below the plate 301. The zero position of the X-cursor block 309 is controlled by an electro-optical sensor 319.

The X-cursor block 309 is provided with a tab 321, which interrupts the light path of the sensor 319 when that cursor 309 moves to the zero position. The zero position of the Y-cursor 310 block is controlled by another electro-optical sensor 320. The Y-cursor block 310 is provided with a tab 321 which interrupts the light path of the sensor 320 when that cursor 310 moves to the zero position. In addition, the position of the sample plate storage compartment 202 of the Y-cursor block 310 is controlled by an electro-optical sensor 322. The light path of the sensor is interrupted when the Y-cursor block 310 moves to the sample plate holder compartment 202 position. In this position, the pivots 304 of the transportation block 303 are concentric with the pivot holes 38 of the sample plate holders which are in the storage compartment 202.

The upper and lower detector assemblies 410 and 420 are provided with aperture plates 411 and 421, respectively, disposed in front of photomultiplier tubes 430 of the detector assemblies. The aperture plate 411 of the upper detector assembly 410 is not shown, but it is exactly a mirror image of the aperture plate 421 of the lower detector assembly 420. The aperture plates are provided with circular aperture holes 422 and 423 corresponding to the diameters of the wells in the 96-well or 24-well sample plates, respectively.

Figure 12:
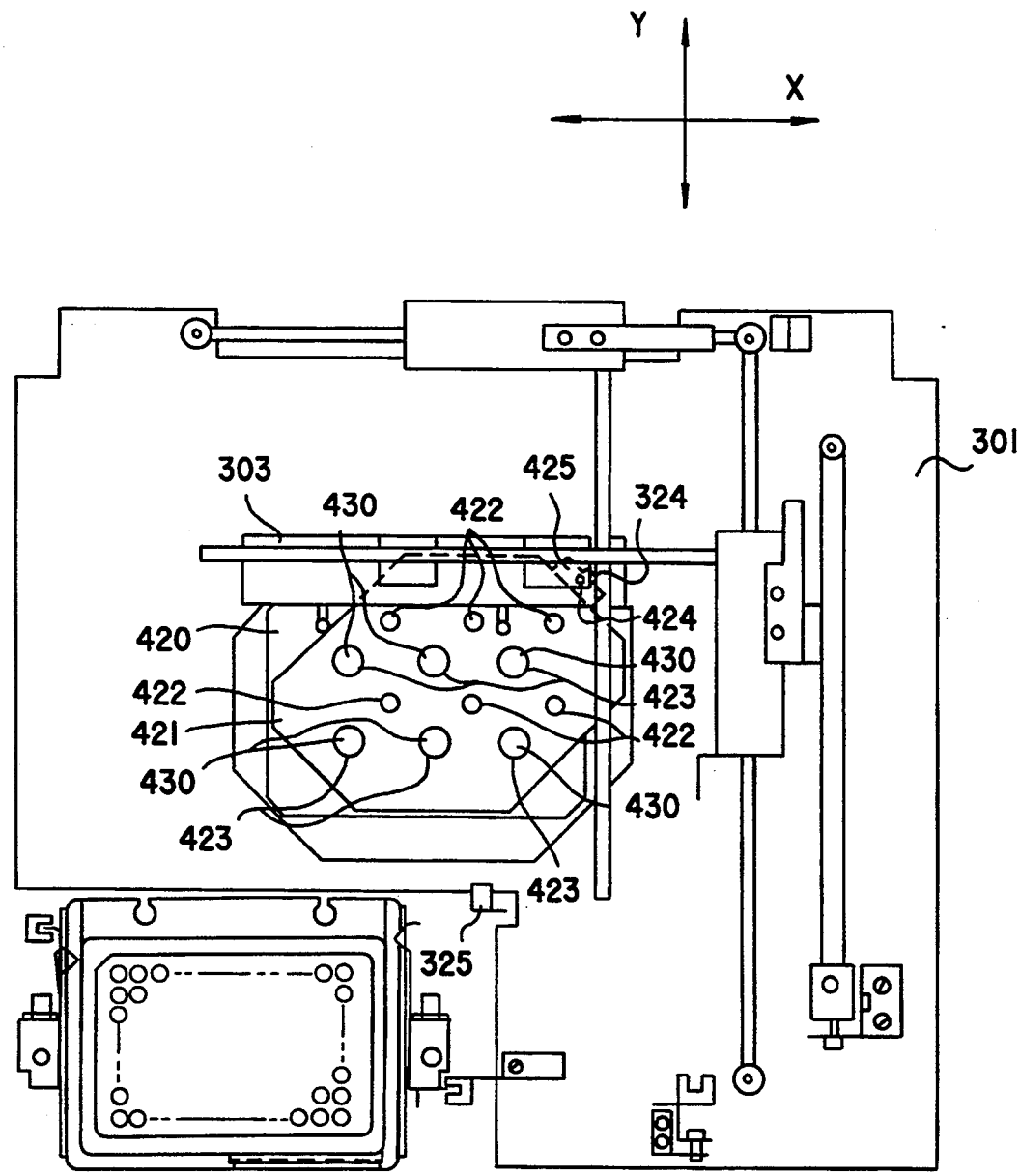
FIG. 12 is a top view of the x-y-transportation system of the apparatus showing the transportation block in a position for changing the aperture holes for 24-well plates to the aperture holes for 96-well plates.
Figure 13:
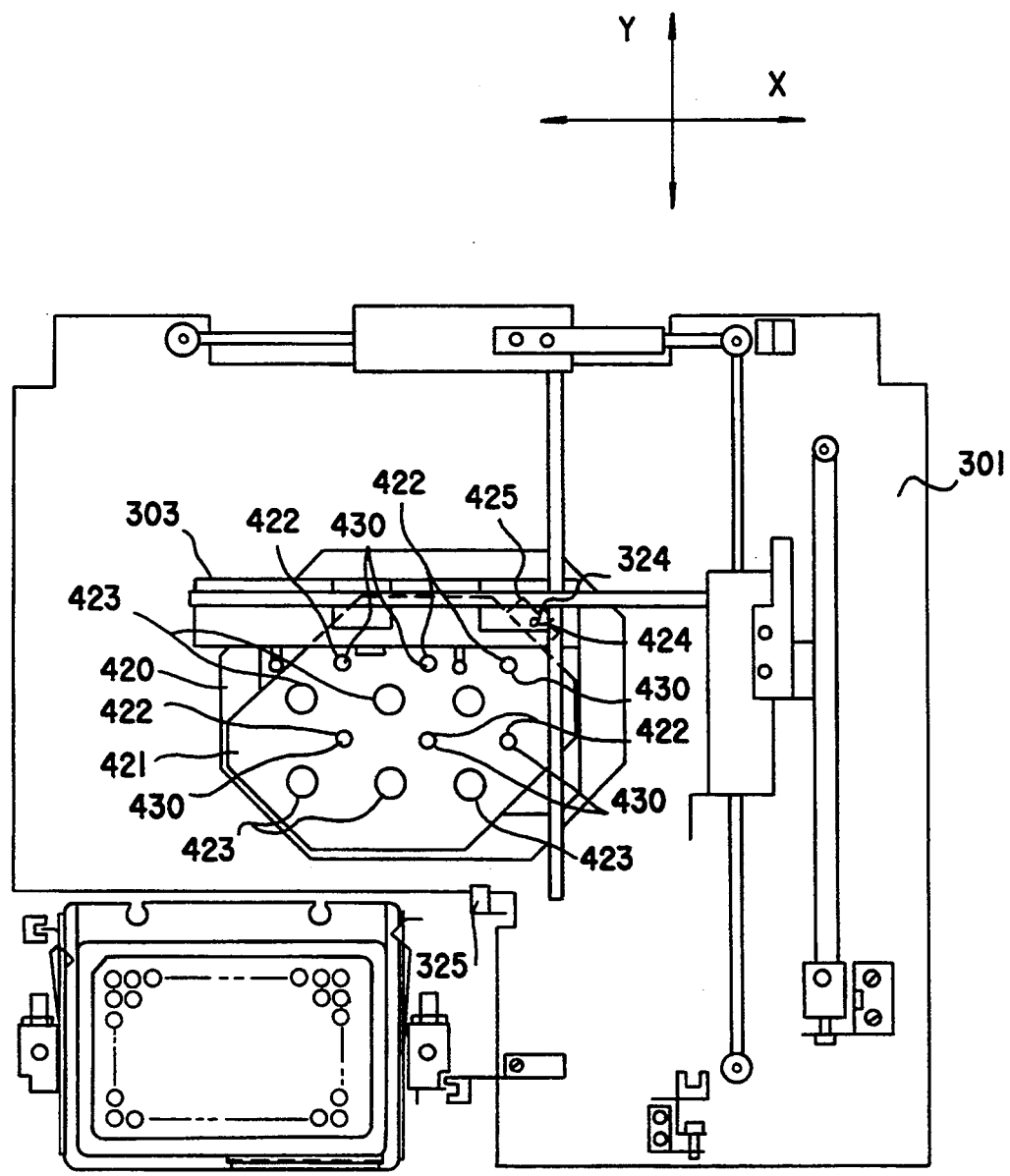
FIG. 13 is a top view of the x-y-transportation system of the apparatus showing the transportation block in a position for changing the aperture holes for 96-well plates to the aperture holes for 24-well plates.

When the x-y-transportation means or system takes the sample plate holder from the storage compartment 202 by the means of the transportation block 303, the control system of the apparatus first checks if the sample plate holder is adapted to 96- or 24-well sample plates. The checking happens so that the transportation block 303 with the sample plate holder moves in the direction of the Y-axis until the slot 36a of the sample plate holder 30a for 96-well sample plate or the slot 36b of the sample plate holder 30b for 24-well sample plate engage with the angular part of the spring tab 225. When this happens the edge 226 of the spring tab 225 interrupts the light path of the electro-optical sensor 224. Because the distances X and Y of slots 36a and 36b from the rear surface of the sample plate holders 30a and 30b are different, the control system detects the type of sample plate holder. If the positions of the aperture plates 411 and 421 do not correspond to the type of the sample plate holder, the x-y-transportation means returns the sample plate holder to the storage compartment 202 and changes the positions of the aperture plates 411 and 421 to correspond to the sample plate holder type. The control system of the apparatus moves the transportation block 303 to a position such that the spring loaded pin 324 is concentric with the pin holes 424 of the ledges 425 of the aperture plates 421 and 411 (FIG. 12a). Next, the upper detector assembly 420 moves downwards until the spring loaded pin 324 of the transportation block 303 engages with the pin holes 424 of both aperture plates 411 and 421. After this, the control system of the apparatus moves the transportation block 303 with attached aperture plates to a new position shown in FIG. 13 so that the aperture holes 422 or 423 correspond to the well diameters of the sample plate. In this example the first position of the aperture plates 421 was such that the aperture holes 423 for the 24-well sample plates were concentric with the photocathodes of the photomultiplier tubes 430 of the upper and lower detector assembly 410, 420 and the second position of the aperture plates 421 shown in FIG. 13 was such that the aperture holes 422 for the 96-well sample plates were concentric with the photocathodes of the photomultiplier tubes 430. It should be understood that this operation should happen as well in the opposite direction in moving from the position shown in FIG. 13 to the position shown in FIG. 12.

When the control system of the apparatus has determined that the positions of the aperture plates 411 and 421 correspond to the type of the sample plate holder 30a or 30b, the transportation means moves the sample plate holder 30a or 30b carrying the sample plate 10 or 20 by the means of the transportation block 303 past an electro-optical reader 325 which reads the bar code labels attached on the ID support plate 42 of the sample plate holder 30a or 30b. The bar code labels convey information to the control system of the apparatus for controlling the operation of the apparatus, for example, which measuring parameters should be used. After this, the apparatus moves the sample plate holder 30a or 30b carrying the sample plate 10 or 20 to the measuring station formed by the upper and lower detector assemblies 410 and 420 shown in FIGS. 15 and 16.

The apparatus of the instrument is provided with 1, 2, 3 or 6 detectors. Each detector having a pair of simultaneously operating photomultiplier tubes mounted in two detector assemblies 410 and 420 shown in FIGS. 9, 15 and 16. The upper detector assembly 410 is adapted to move in the vertical direction in order to permit various heights of multi-well sample plates to be used. Both detector assemblies 410 and 420 are provided with aperture plates 411 and 421, respectively, having circular apertures 422 and 423 in front of the photocathodes of the photomultiplier tubes 430 for 96-well sample plates 10 and 24-well sample plates 20.

The 6 places of the photomultiplier tubes 430 are arranged in 2 rows with 3 columns having 36 millimeters spacing between the center points, as shown for example in FIG. 11, for the lower detector assembly 420. When the apparatus is provided with one detector, the photomultiplier tube 430 of the lower detector assembly 420 is positioned on the first column of the first row (position 441). The photomultiplier tube 430 of the upper detector assembly 420 is positioned on the corresponding place so that simultaneously operating photomultiplier tubes 430 are concentric. When the apparatus is provided with 2 detectors, the photomultiplier tubes 430 of the lower detector assembly 420 are positioned on the first columns of the first and the tubes 430 of the upper detector assembly 410 are positioned on the corresponding places. When the apparatus is provided with 3 detectors, the photomultiplier tubes 430 of the lower detector assembly 420 are positioned on the first row (positions 441, 442 and 443) and the photomultiplier tubes 430 of the upper detector assembly 410 are positioned on the corresponding places. This detector arrangement permits the matrix format and well separation of 96-well sample plate 10 and 24-well sample plate 20 and corresponding sample plates when the apparatus is provided 1, 2, 3 or 6 detectors. Naturally, a sample plate having 6 sample wells with 36 millimeters separation is allowed. In general, if the distance of the center points of the detector positions is d, then the allowed distances of the center points of the sample wells of the sample plates should be d/n, where n=1, 2, 3, ....

Figure 14:
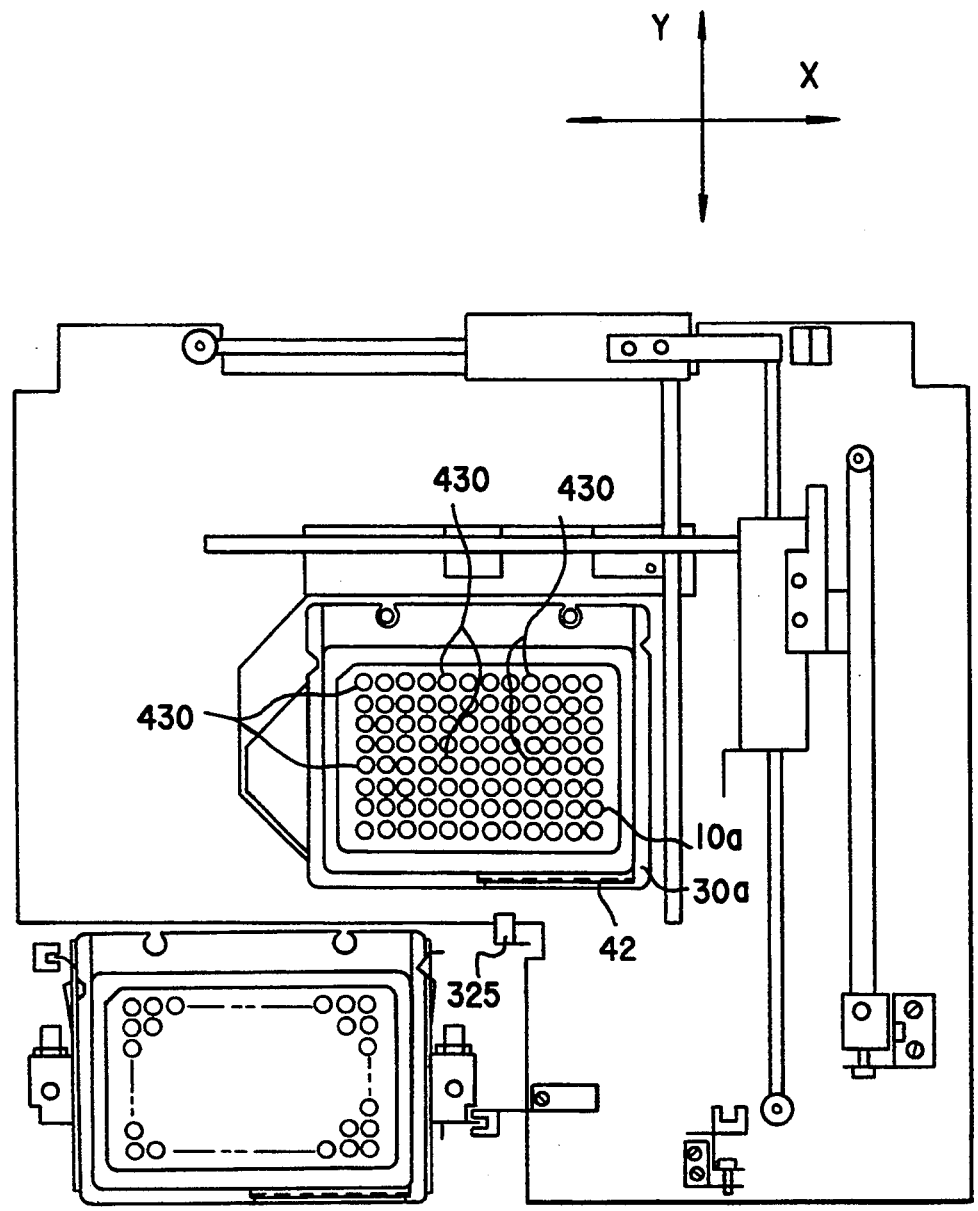
FIG. 14 is a top view of the x-y-transportation system of the apparatus showing a 96-well sample plate in the first measuring position.

In FIG. 14 there is a 96-well sample plate 10 carried by the corresponding sample plate holder 30a stopped in the first measuring position. In this position the first, the fifth and the ninth sample wells of the first and the fifth rows of the sample plate 10 are measured if the apparatus is provided with six detectors. (If the sample plate is 24-well 20, when the first, the third and the fifth sample wells of the first and the third rows are measured.) When the apparatus has measured these sample wells, the transportation means moves the sample plate holder 30a or 30b carrying the sample plate 10 or 20 to the second measuring position and so on until the whole sample plate is measured. After measurement, the sample plate with the sample plate holder is moved back to the storage compartment 202 and the next sample plate holder, whose position is defined by the control means of the apparatus according to the selection of the user, is moved past the ID reader 325 to the counting station.

Figure 15:
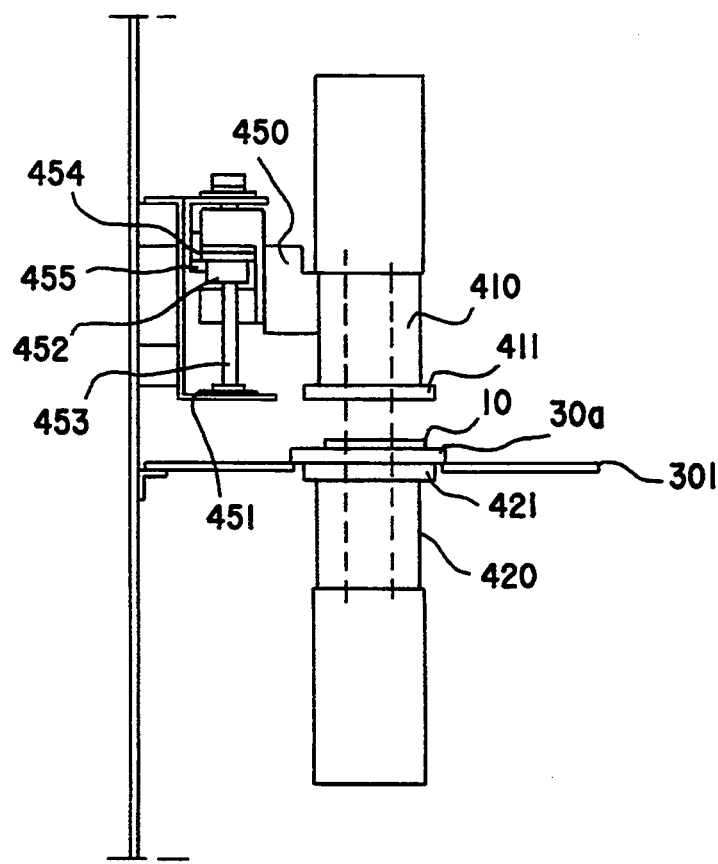
FIG. 15 is a side view of the measuring station of the apparatus showing the upper detector assembly in the upper position.
Figure 16:
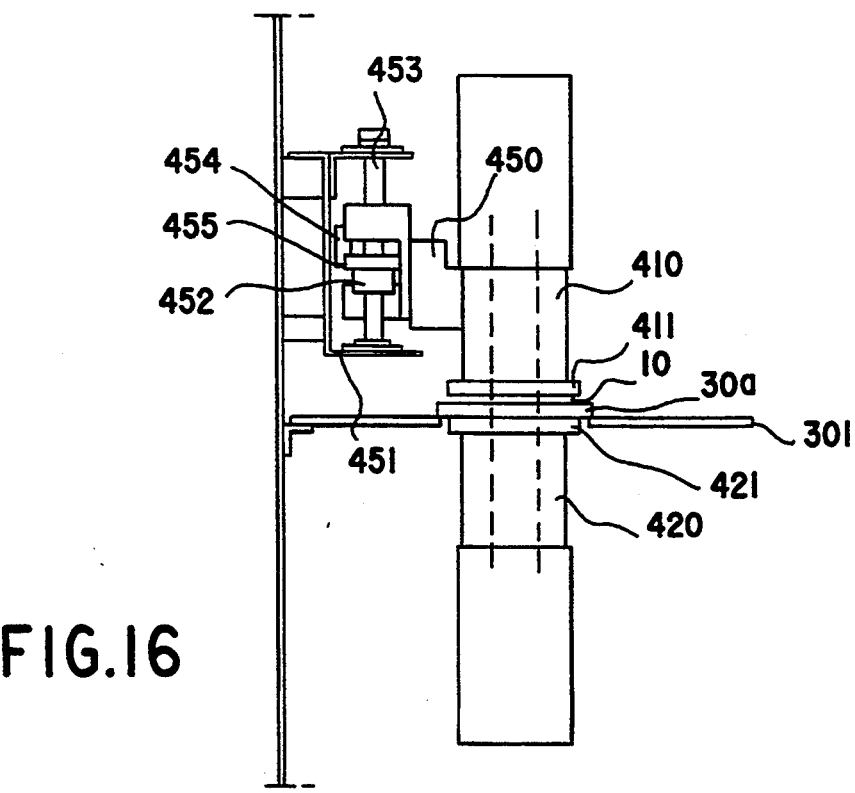
FIG. 16 is a side view of the measuring station of the apparatus showing the upper detector assembly in the measuring position.

In FIGS. 15 and 16 are shown the movement of the upper detector assembly 410. When the transportation block is moving the upper detector assembly is in the up position shown in FIG. 15. When the sample plate holder 30a or 30b with sample plates 10 or 20 is in the measuring position the upper detector assembly moves downwards until it touches the sample plate 10 or 20 carried by the sample plate holder 30a or 30b. The upper detector assembly 410 is adapted to stop in any position so as to accommodate the different heights of the sample plate holders. The upper detector assembly is mounted on a support block 450 which can travel along two vertical rods (not shown) attached on the base support member 451. The support block 450 hangs on a travel member 452 by a threaded coupling so that it is mounted on an elongated threaded lead screw 453 driven by a stepper motor (not shown). The support block 450 is provided with an electro-optical sensor 454 and the travel member 452 with a tab plate 455 for interrupting the light path of the electro-optical sensor 454 when the support block 450 hangs on the travel member 452. If the upper detector assembly 410 is disabled to move with the travel member 452, the travel member 452 with the tab plate 455 continues its motion downwards until it separates from the support block 450 so that the tab plate 455 finishes the interruption of the light path of the electro-optical sensor 454.

The apparatus according to the present invention is not confined to the above embodiments alone, but it may show even considerable variation within the scope of the patent claims.

What is claimed is:

1. Apparatus for counting liquid scintillation samples in sample plates of a preselected assortment of different multi-well sample plate types, each type having a two dimensional array of sample wells, said apparatus including a counting station comprising at least one detector, each detector provided with two vertically positioned photomultiplier tubes, mounted in two detector assemblies, where at least an upper assembly is movable in a vertical direction, wherein:

said apparatus is provided with a transportation system for transporting said different multi-well sample plate types belonging to said preselected assortment, said transportation system comprises a plurality of different types of sample plate holders, for carrying said different multi-well sample plate types belonging to said preselected assortment, said sample plate holders provided with registration means for distinguishing said different types of sample plate holders, said different types of sample plate holders being coupled with said transportation system, and said different types of sample plate holders provided with equivalent sample plate identification means having a detachable support plate associated with each of said sample plate holders, at least one bar code label attachable on said support plate.

2. Apparatus according to claim 1, wherein said transportation system comprises a random access sample plate holder storage compartment having at least one position for said sample plate holders, a stepper motor and an electro-optical sensor system, said sample plate holder storage compartment movable in the vertical direction and driven by said stepper motor and controlled by said electro-optical sensor system.

3. Apparatus according to claim 2, wherein said transportation system comprises a transportation means including a transportation block for moving said sample plate holders in a horizontal plane, said horizontal plane being associated with said sample plate holder storage compartment, said transportation block being coupleable with any one of said sample plate holders.

4. Apparatus according to claim 3, wherein the transportation means is provided with an electro-optical reader in said horizontal plane for reading said at least one bar code label attached on the detachable support plates associated with said sample plate holders.

5. Apparatus according to claim 3, wherein the transportation means is provided with two stepper motors in said horizontal plane for driving said transportation means and two electro-optical sensors for controlling a zero position of said transportation means and one electro-optical sensor for controlling a coupling position of said sample plate holders in said storage compartment.

6. Apparatus for counting liquid scintillation samples in sample plates of a preselected assortment of different multi-well sample plate types, each type having a two dimensional array of sample wells, said apparatus including a counting station comprising at least one detector, each detector provided with two vertically positioned photomultiplier tubes, mounted in two detector assemblies, where at least an upper assembly is movable in a vertical direction, wherein:

said apparatus is provided with a transportation system for transporting said different multi-well sample plate types belonging to said preselected assortment, said transportation system comprises a plurality of different types of sample plate holders, for carrying said different multi-well sample plate types belonging to said preselected assortment, said sample plate holders provided with registration means for distinguishing said different types of sample plate holders, said different types of sample plate holders being coupled with said transportation system, said different types of sample plate holders provided with equivalent sample plate identification means having a detachable support plate associated with each of said sample plate holders, at least one bar code label attachable on said support plate, said transportation system including a transportation means comprising a transportation block for moving said sample plate holders in a horizontal plane, said horizontal plane being associated with a sample plate holder storage compartment, said transportation block being coupleable with any one of said sample plate holders, wherein said detector assemblies are provided with aperture means comprising a plurality of apertures for different well diameters of said multi-well sample plates, and said aperture means are switched by moving said transportation block to correspond to different well diameters of said different multi-well sample plate types.

7. Apparatus according to claim 6, wherein said transportation means takes one sample plate holder at a time from said sample plate holder storage compartment and transports it to said counting station and moves said sample plate holder in proportion to said counting station in order to enable counting of each sample well of the multi-well sample plate.

* * * * *